United States Patent [19]

Suciu et al.

[11] Patent Number: 4,691,031

[45] Date of Patent: Sep. 1, 1987

[54] PROCESS FOR PREVENTING BACKMIXING IN A FLUIDIZED BED VESSEL

[76] Inventors: George D. Suciu, 417 Prospect St., Ridgewood, N.J. 07450; John E. Paustian, 38 Adams Dr., Whippany, N.J. 07981

[21] Appl. No.: 622,767

[22] Filed: Jun. 20, 1984

[51] Int. Cl.$^4$ ............................................. B01J 8/18
[52] U.S. Cl. ..................................... 549/258; 34/10; 34/57 A; 422/141; 422/142
[58] Field of Search ............... 422/142, 144, 146, 141; 34/10, 57 A; 432/15, 57; 423/DIG. 16; 549/262, 258; 431/7, 170

[56] References Cited

U.S. PATENT DOCUMENTS

| | | |
|---|---|---|
| 2,702,267 | 2/1955 | Keith ..................................... 422/142 |
| 3,482,946 | 12/1969 | Shirk ..................................... 422/142 |
| 3,754,993 | 8/1973 | Oguchi et al. ....................... 422/141 |
| 3,783,528 | 1/1974 | Shedig ................................. 422/141 |
| 3,793,444 | 2/1974 | Reeves et al. ....................... 423/502 |
| 3,910,849 | 10/1975 | Kawabata et al. ............... 422/141 X |
| 3,980,439 | 9/1976 | Mayer ............................... 422/145 X |
| 4,311,670 | 1/1982 | Nieminen et al. ................... 422/145 |

FOREIGN PATENT DOCUMENTS 0000009  1/1979  PCT Int'l Appl. ................. 422/141

Primary Examiner—Barry S. Richman
Assistant Examiner—William R. Johnson
Attorney, Agent, or Firm—Elliot M. Olstein

[57] ABSTRACT

A process for preventing backmixing in a fluidized bed vessel wherein a gaseous fluid phase and fluidized solids are moved co-currently through a plurality of fluid bed compartments in substantially plug flow. The vessel may be used for production of maleic anhydride.

8 Claims, 2 Drawing Figures

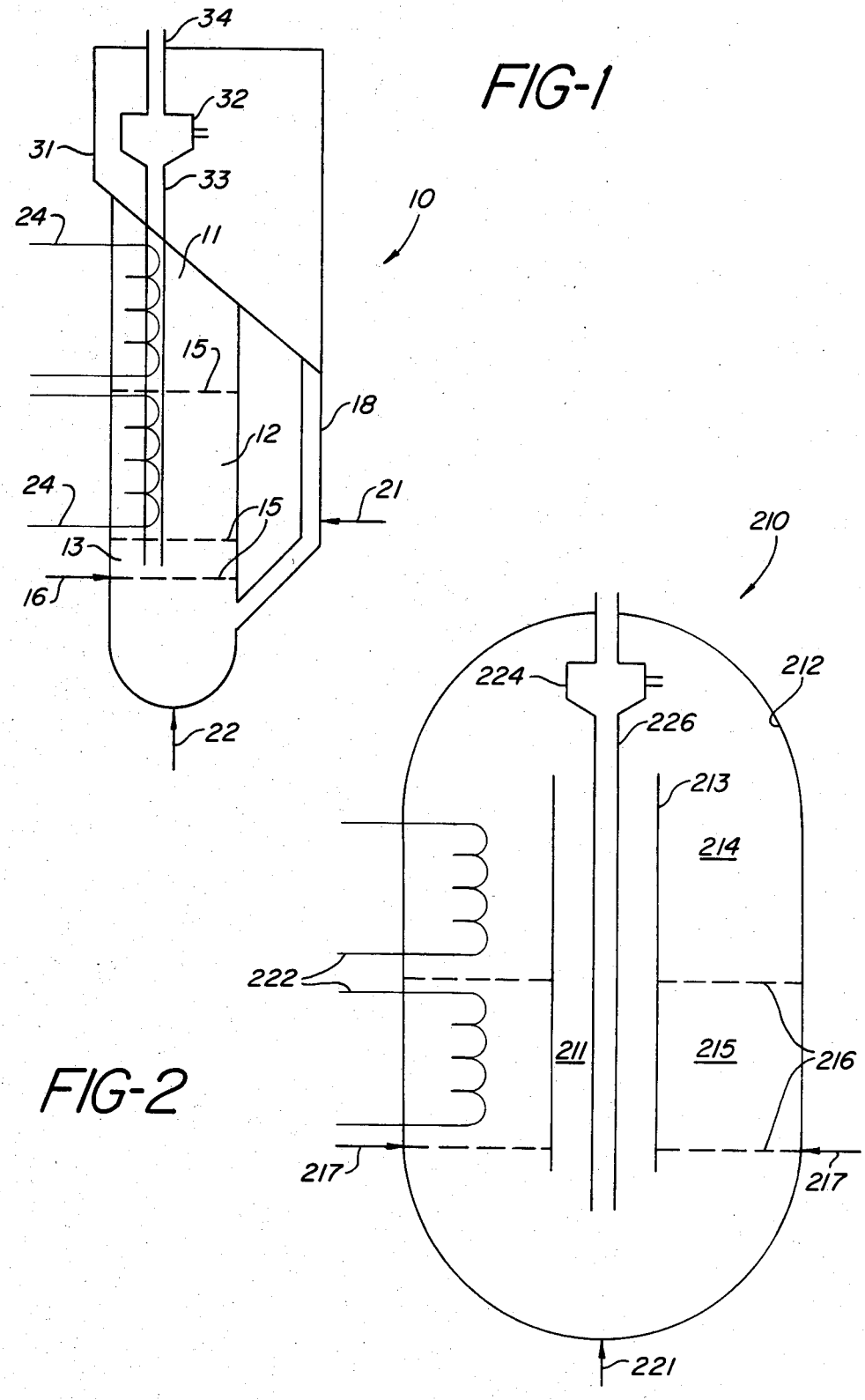

PROCESS FOR PREVENTING BACKMIXING IN A FLUIDIZED BED VESSEL

This invention relates to a fluidized bed, and the use thereof for contacting a fluid phase with solid particles.

This invention further relates to a new and improved process for effecting a reaction in a fluidized bed.

This invention additionally relates to the production of maleic anhydride in a fluidized bed.

Fluidized beds are generally known in the art as being suitable for effecting contact between a fluid phase and solids. In particular, such fluidized beds are known to be suitable for effecting catalytic reactions wherein one or more fluid reagents are contacted with a particulate solid catalyst.

In using fluidized beds for effecting catalytic reactions, it is known that the solids and fluid phase (both reagents and product) exist in a well mixed state, with some of the products being recirculated throughout the bed. This back circulation, also known as back-flow or back-mixing, prolongs the contact time between the product and catalyst, which may result in excessive degradation of the product.

In order to solve the problem of back-mixing, it has been proposed, for example, in U.S. Pat. No. 3,482,946, and U.S. Pat. No. 3,783,528, to provide the fluidized bed reactor with compartments or stages; for example, by providing horizontal baffling, so as to minimize back-mixing of the fluid phase between compartments or stages, while retaining the other advantages which are inherent in the use of a fluidized bed of solids.

In such reactors, in the individual compartments, the solids and the fluid phase are well mixed (back-mixed); however, the fluid phase moves in one direction (no back-mixing between compartments) so that the fluid phase approaches plug flow between the compartments. In such reactors, the fluidized solids are free to move between compartments in either direction or such fluidized particles remain confined within individual compartments.

The present invention is directed to an improvement in a fluidized bed contact zone, which has particular applicability to fluidized bed reactors. Moreover, this invention further relates to an improved process for producing maleic anhydride in a fluidized bed reactor.

In accordance with one aspect of the present invention, there is provided a process for contacting a fluid phase (gas and/or liquid) with solid particles in a fluidized bed divided into at least two compartments or stages, with the solid particles being maintained as a fluidized bed in each of the compartments and both the fluid phase and the fluidized particles moving cocurrently through successive compartments in substantially plug flow. In each compartment or stage the fluidized particles and fluid phase are well mixed (back-mixing); however, at the scale of the overall bed both the fluidized solids and the fluid phase move cocurrently through the fluidized bed in substantially plug flow.

In order to prevent an accumulation of solid particles in the last compartment or stage, solid particles are separated from the fluid phase and are returned to an initial compartment or stage.

In accordance with another aspect of the present invention, there is provided a fluidized bed vessel for contacting a fluid phase with solid particles which includes partition means for dividing the vessel into at least two fluidized bed compartments or stages, with the partition means including an open (free) area to permit flow between the compartments or stages, which is coordinated with other parameters in a manner such that the solid particles are in the form of a fluidized bed in each compartment and both the fluidized phase and the fluid particles move co-currently through successive compartments in substantially plug flow. The vessel is further provided with passage means for returning solid particles from the last compartment or stage to an initial compartment or stage.

In accordance with the present invention, various parameters are controlled so as to provide for a fluidized bed in each compartment or stage and co-current movement of both the fluidized solids and fluid phase in substantially plug flow between the compartments or stages.

More particularly, the linear velocity of the fluid phase in each compartment is a multiple of the minimum fluidization velocity of the solid particles, but less than the entrainment velocity of the particles.

The free area of the partition(s) through which fluid and fluidized particles flow between compartments is smaller than the free area available for flow in the compartments or stages such that the linear velocity of the fluid phase through the partition exceeds the entrainment velocity of the solid particles. In this manner, particles are entrained for movement between compartments in the direction of flow of the fluid phase, and the fluid velocity opposes flow of solid particles in the opposite direction, whereby the fluidized soids move co-currently with the fluid phase in substantially plug flow. An excessive velocity through the partition is generally avoided so as to avoid unnecessary pressure drop and an increase in the rate of catalyst attrition.

In general, the linear velocity of the fluid phase in the compartments is from 2 to 50 times higher than the minimum fluidization velocity, and the linear velocity of the fluid phase through the free area of the partition(s) is 0.8 to 2.0 times higher than the entrainment velocity of the solid particles. In most cases, the linear velocity of the fluid phase through the partition does not exceed 100 to 150 feet per second so as to avoid excessive pressure drop and mechanical attrition of particles. In most cases, the flow area (cross-section) through the partitions is 20% to 60% of the flow area (cross-section) through the compartments or stages.

It is to be understood that the above conditions although preferred, may be varied within the spirit and scope of the invention.

The fluid phase which is passed through the bed may be a gas phase and/or liquid phase, and the gas and/or liquid phase(s) may be comprised of one, two or more components.

The solid particles are maintained as a fluidized bed and may be any one of a wide variety of particles which are conventionally employed in fluidized beds.

In accordance with a preferred embodiment, the fluidized bed is employed as a reactor, and the fluidized bed of solids within the reactor is comprised of solid catalyst particles.

As hereinafter indicated, such fluidized bed reactor is particularly suitable for effecting exothermic reactions, and in particular, an exothermic reaction for producing maleic anhydride.

Thus, by proceeding in accordance with one aspect of the present invention, there is provided a vessel containing a fluidized bed of solids, with the vessel having superimposed fluidized bed compartments, with there being mixing of the fluidized particles and fluid phase in each compartment, without back-mixing of the particles and fluid phase between the compartments. The fluidized particles and fluid phase move upwardly through the superimposed compartments in substantially plug-flow, with the particles being passed from an upper portion of the vessel, to a lower portion of the vessel, externally of the fluidized beds.

The invention will be further described with respect to the accompanying drawings, wherein:

FIG. 1 is a section view in elevation of one embodiment of a fluidized bed vessel in accordance with the invention; and FIG. 2 is a section view in elevation of another embodiment of a fluidized bed vessel in accordance with the invention.

It is to be understood, however, that the scope of the invention is not to be limited by the embodiments specifically shown in the drawings.

Referring now to FIG. 1 of the drawings, there is shown a vessel, schematically generally indicated as 10, which is a fluidized bed vessel; and in particular, a fluidized bed reactor.

The reactor is divided into superimposed fluidized bed compartments 11, 12 and 13. As particularly shown, the compartments 11, 12 and 13 are formed by partitions having a free area for permitting flow between the compartments in the form of grids 15 at the bottom of each compartment.

Although the embodiment shown in FIG. 1 employs a plurality of grids 15 for maintaining superimposed fluidized bed compartments in vessel 10, it is possible within the spirit and scope of the invention to replace the perforated plates or grids 15 with suitable baffling. As hereinabove indicated, the partitions function to reduce the cross-section of the vessel at spaced intervals so as to provide superimposed fluidized beds and co-current flow of the fluidized solids and fluid phase between the beds in substantially plug flow.

The fluid phase for contacting the solid particles in the fluidized bed; in particular, a reaction feed, is introduced into the bottom portion of the reactor through line 16.

Vessel 10 is further provided with a solid return line 18 for returning solids from an upper portion of the vessel 10; namely, compartment 11, to a lower portion of the reactor for introduction into the lower compartment 13.

The return leg 18, as well as the bottom portion of the vessel 10 are provided with means for introducing a gas into the return line and vessel in the form of inlet lines 21 and 22, respectively. The introduction of gas through line 21 prevents bridging of particles in return line 18 so as to ensure downward flow of the particles through return line 18. The introduction of gas through line 22 maintains movement of solids in the bottom of the vessel i.e. a static condition is eliminated which would prevent flow. Thus, the recirculation rate can be controlled by controlling gas introduction through line 22.

The gas introduced through lines 21 and 22 may be feed or air. In the absence of the introduction of such gas, flow of solids through the return line would be stopped by a bed of solids in the bottom of vessel 10.

The compartments 11 and 12 are further provided with means for introducing or withdrawing heat from the compartments, as required, in the form of heat transfer coils 24 for passing a heat transfer fluid in an indirect heat transfer relationship with the solids in the compartment.

The heat transfer coils 24 in each of the compartments may be maintained at different temperatures so as to appropriately regulate the temperatures in the compartments 11 and 12. The vessel is preferably employed for accomplishing an exothermic reaction, and as a result, the heat transfer coils 24 are provided with a cooling fluid so as to aid in maintaining proper temperatures through the length of the reactor. Heat transfer coils could be omitted and/or also added to compartment 13 and/or used in different compartments than as shown.

As hereinabove indicated, the cross-section of the area vailable for flow in each of the compartments 11, 12 and 13 is coordinated with the cross-section available for flow through the partitions 15 as well as the size of the solid particles and the flow rate of the fluid phase so that the fluidized particles and fluid phase are well mixed (back-mixed) in each compartment 11, 12 and 13, and the fluid phase and fluid particles flow co-currently upwardly through successive compartments 13, 12 and 11 in substantially plug flow.

The major portion of the particles are separated from the fluid phase at the top of compartment 11 and are returned to the bottom of the reactor through line 18. The rate of recirculation through line 18 is primarily controlled by the rate of gas introduction through line 22, and in part, by the rate of gas introduction through line 21.

The fluid phase is withdrawn from vessel 10 through a cyclone separator 32 to remove any particles entrained in the fluid phase, with such entrained particles being returned to the bottom of the vessel 10 through leg 33. Fluid phase free of entrained particles is withdrawn through line 34.

Although the vessel 10 has been described with respect to three superimposed compartments, the vessel could be provided with two compartments or more than three compartments.

A further embodiment of a fluidized bed vessel of the present invention is shown in FIG. 2.

Referring to FIG. 2, there is shown a fluidized bed vessel 210 in which the interior of the vessel 210 is divided into a central portion 211 and an annular portion 212 by a cylindrical baffle 213. As particularly shown, the central portion 211 is used as a solids return line, and the annular portion 212 is used for a fluidized bed of solids.

Annular portion 212 is divided into annular superimposed compartments 214 and 215 by a pair of axially spaced distributor grids 216 which function as hereinabove described to provide spaced compartments and co-current flow of the fluid phase and fluidized particles in substantially plug flow.

The fluid phase which is to be introduced into the vessel 210 for contact with the solid particles in the fluidized bed; in particular, a reaction feed, is introduced into the bottom of the annular portion through inlet lines 217.

In the embodiment of FIG. 2, the central portion 211 functions for returning solids from an upper portion of the vessel 210 to a lower portion of the vessel 210. Gas is introduced into the bottom of vessel 210 through an inlet line 221 to insure recirculation through central portion 211; i.e., the gas creates movement (aeration) of solids in the bottom of vessel 210 to prevent static conditions which would inhibit (or prevent) flow through central portion 211.

In addition, the compartments 214 and 215 are provided with heat exchange coils 222 for controlling temperature in the compartments.

The vessel 210 is further provided with a cyclone 224, fluid outlet line 225 and return leg 226 for returning separated fines to the bottom of the vessel 210.

The vessel shown in FIG. 2 operates in a manner similar to the previous embodiments, with the fluid phase and solids moving upwardly in substantially plug flow through the annular compartments 215 and 214, with the solids then being returned to the bottom portion of the vessel 210 through the central portion 211.

The embodiment of FIG. 2 may also be modified in a manner such that the fluidized bed is maintained in the central portion of vessel 210 and the annular portion is employed for returning solids from an upper portion of the vessel 210 to the lower portion.

As hereinabove indicated, the fluidized bed vessel of the present invention may be employed for effecting contact between a wide variety of solids and fluids; however, the vessel has particular applicability as a fluidized bed reactor wherein one or more reactants are contacted with a solid catalyst. The fluidized bed reactor has particular applicability to exothermic reactions; and in particular, to the production of maleic anhydride.

Other such exothermic reactions to which the present invention can be applied include: hydrogenations, oxychlorinations, ammonolyses and ammoxidation, oxidation, and vapor phase nitrations. Specific processes illustrative of these may include the formation of acrolein and/or acrylonitrile from propylene; aromatic nitriles from alkyl aromatics, such as phthalonitrile from xylenes, nicotinonitrile from alkyl pyridines; ethylene oxide from ethylene, etc.

The present invention will be further described with respect to the production of maleic anhydride from n-butane; however, as known in the art, saturated or unsaturated $C_4$ to $C_{10}$ hydrocarbons or mixtures thereof, other than n-butane, may be employed as a feed for producing maleic anhydride; for example, 1,3-butadiene or a $C_4$ cut from a refinery.

Conditions under which maleic acid may be produced using the reactor of the present invention are: temperature, 350° C. to 475° C., particularly 390° C. to 420° C. Although a flat (i.e., uniform) temperature profile along the length of the reactor is desired, in some situations, a smoothly changing profile may be desired and is achievable by the present invention. Whereas in the oxidation of n-butane to maleic anhydride in a fixed bed reactor the temperature of a hot spot can exceed by approximately 50° C. or more the temperature which prevails in the rest of the reactor, by the technology of the present invention, the temperature along the reactor can be kept constant within 5°–15° C. or can be adjusted at will by means of the heat exchanger devices allocated to each compartment.

The concentration of hydrocarbon (butane) in air is generally 1 to 20 volume percent, or higher, particularly 2–8 volume percent. The linear velocity in the free area of the compartments (at reaction temperature), is 0.5 to 10 ft/sec.; particularly, 1 to 4 ft/sec. The catalyst used may be any typical maleic anhydride catalyst, particularly one containing vanadium and phosphorous as known in the art.

The catalyst particle size distribution will be typical of those used in fluid bed processing with an average particle size of 40 to 500 microns, preferably 80–150 microns.

The invention will be further described with respect to the following examples; however, the scope of the invention is not to be limited thereby:

EXAMPLE 1

Oxidation of n-butane to maleic anhydride (MA) is carried out in a reactor having a configuration similar to that depicted in FIG. 1, made of stainless steel. The reactor has a diameter of 2", the expanded zone of 4 and the return line of 1". The bed height is 4 ft. The reactor volume is divided into a succession of compartments by means of horizontal baffles (made of stainless steel mesh screens) which have a free cross-sectional area of 30%.

In normal operation the upper level of the fluidized bed is at or above the top opening of the return line. Catalyst overflows into this and is returned in dense phase flow to the bottom of the fluid bed.

The reactor is provided with external electrical heating along its length, operated via a thermostating device which controls the outer wall temperature. A travelling thermocouple placed axially allows one to read the temperature profile along the bed. The return line is provided with two aeration taps by which the catalyst flow can be controlled.

An air stream of 19 l/min containing 5.2 vol % n-butane was fed through a sparger to the bottom of the reactor. Approximately 100 cc l/min air is fed through each aeration tap so that a smooth catalyst circulation is achieved. The temperature along the bed length was 403±1° C. The conversion of n-butane was 58.7% and the molar selectivity to Maleic Anhydride was 61.1%.

EXAMPLE 2

(not according to this invention)

The same setup as in Example 1 is used. No aeration gas is provided to the catalyst return line. The catalyst circulation in this line is thus stopped.

By using the same feed flow rates, and the same setting for the temperature controller as in Example 1, the conversion of butane is 50.0% and the molar selectivity to MA is 60.1%. An axial temperature scan indicated a difference of approximately 40° C. between the upper and lower ends of the reactor.

The invention is particularly advantageous in that as compared to fluidized vessels and methods of the prior art, better temperature control can be achieved. In addition, the size of the vessel can be reduced for the same overall capacity. The present invention provides the desired characteristics of a plug flow reactor, while retaining the advantages of a fluidized bed reactor.

These and other advantages should be apparent to those skilled in the art from the teachings herein.

Numerous modifications and variations of the present inventon are possible in light of the above teachings and, therefore, within the scope of the appended claims, the invention may be practiced otherwise than as particularly described.

What is claimed is:

1. A process for reacting a fluid phase in contact with solid catalyst particles in a fluidized bed contact zone, comprising:
    reacting the fluid phase in contact with solid catalyst particles in a fluidized bed vessel including at least two fluidized bed compartments defined by partition means including a free flow area whereby said at least two fluidized bed compartments are in fluid flow communication with each other; maintaining the solid catalyst particles as a fluidized bed in each of the at least two compartments; passing the fluid phase through each of the compartments at a linear velocity of 2 to 50 times greater than the minimum fluidization velocity for the solid catalyst particles; passing the fluid phase through the free area of the partition means at a linear velocity of from 0.8 to 2.0 times greater than the entrainment velocity of the solid catalyst particles to thereby pass both the fluid phase and solid catalyst particles co-currently between the at least two fluidized bed compartments in substantially plug flow; separating solid catalyst particles from the fluid phase after passage through the at least two compartments; and recycling the separated solid catalyst particles for passage through the at least two compartments.

2. The process of claim 1 wherein the at least two compartments are superimposed above each other and the fluid phase and solid particles move upwardly through the at least two compartments.

3. The process of claim 1 wherein the free flow area of the partition means is from 20% to 60% of the flow area in the compartment.

4. The process of claim 1 wherein the fluid phase is a gas.

5. The process of claim 4 wherein the gas is comprised of a $C_4$ to $C_{10}$ hydrocarbon and oxygen, the solid catalyst is an oxidation catalyst and maleic anhydride is produced in the process.

6. The process of claim 5 wherein the catalyst particles have an average particle size of from 40 to 500 microns.

7. The process of claim 5 wherein the temperature in the fluidized bed vessel is from 350° C. to 475° C.

8. The process of claim 7 wherein the temperature along the length of the reactor does not vary by more than 15° C.

* * * * *

UNITED STATES PATENT AND TRADEMARK OFFICE
CERTIFICATE OF CORRECTION

PATENT NO. : 4,691,031
DATED : September 1, 1987
INVENTOR(S) : George D. Suciu, et al It is certified that error appears in the above-identified patent and that said Letters Patent is hereby corrected as shown below:

Column 4, line 15, change "vailable" to --available--.
Column 8, line 18, Claim 8, change "reactor" to --vessel--.

Signed and Sealed this

Eleventh Day of July, 1989

Attest:

DONALD J. QUIGG

*Attesting Officer*   *Commissioner of Patents and Trademarks*